US00PP20620P3

(12) United States Plant Patent
Smith

(10) Patent No.: US PP20,620 P3
(45) Date of Patent: Dec. 29, 2009

(54) *ECHINACEA* PLANT NAMED 'CONEVIN'

(50) Latin Name: *Echinacea purpurea*
Varietal Denomination: Conevin

(75) Inventor: M. Nevin Smith, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/153,077

(22) Filed: May 13, 2008

(65) Prior Publication Data

US 2009/0288234 P1 Nov. 19, 2009

(51) Int. Cl.
*A01H 5/00* (2006.01)

(52) U.S. Cl. ..... Plt./428

(58) Field of Classification Search ..... Plt./428
See application file for complete search history.

*Primary Examiner*—June Hwu
(74) *Attorney, Agent, or Firm*—Buchanan Ingersoll & Rooney PC

(57) ABSTRACT

A new and distinct highly ornamental *Echinacea* plant is provided. The flowers are attractive and display deeper red-purple flowers than the 'Magnus' cultivar (non-patented in the United States) which are substantially non-fading and bear substantially horizontal ray florets. An upright branching growth habit is displayed. The plant is well tolerant to heat and drought. The green foliage contrasts nicely with the colorful flowers. The plant is well suited for providing attractive ornamentation when grown in the landscape or during pot culture.

1 Drawing Sheet

Botanical/commercial classification: *Echinacea purpurea/ Echinacea* Plant.

Varietal denomination: cv. 'Conevin'.

SUMMARY OF THE INVENTION

*Echinacea purpurea*, sometimes known as Purple *Echinacea* or Purple Cone Flower, is recognized to be a native American plant found throughout the southeastern portion of the United States. Its growing area commonly is bounded by Michigan and Oklahoma on the west and Virginia, North Carolina and Georgia on the east. This plant commonly can be grown in most soils in U.S.D.A. Hardiness Zone Nos. 3 to 9, and generally displays high tolerance to heat and drought.

The new *Echinacea* plant of the present invention was discovered during 2000 at Suncrest Nurseries, Inc., Watsonville, Calif., U.S.A., while growing in a block of plants of the 'Magnus' cultivar (non-patented in the United States) which had been grown from seed. Accordingly, the new plant was discovered while growing in a cultivated state within a plant nursery. The new cultivar of the present invention is believed to be a chance seedling of unknown parentage. I was primarily attracted to the single plant of the present invention in view of the distinctive appearance of its flowers. Had I not discovered and preserved this plant, it would have been lost to mankind.

The new cultivar has been carefully preserved and has been evaluated to confirm that its characteristics are reliably expressed.

It was found that the new *Echinacea* plant of the present invention displays the following combination of characteristics:

(a) forms attractive deeper red-purple flowers than the 'Magnus' cultivar (non-patented in the United States) which are substantially non-fading and bear substantially horizontal ray florets, (b) displays an upright branching growth habit, and (c) is well suited for providing attractive ornamentation when grown in the landscape and during pot culture.

The new cultivar grows well in most soils of U.S.D.A. Hardiness Zone Nos. 3 to 9, and generally well resists heat and low water growing conditions. The roots are fibrous. One to several multiple-branched stems arise from a crown or caudex.

When compared to other known *Echinacea purpurea* cultivars, the new cultivar of the present invention can be readily distinguished. For instance, when compared to the 'Magnus' cultivar, the new cultivar displays deeper re-purple flowers which do not fade, and bears the ray florets in a substantially horizontal array.

The new cultivar also can be readily distinguished from the 'Rubenstein' and 'Pixie Meadowhite' cultivars (both non-patented in the United States). More specifically, the blossoms of the new cultivar are deeper in coloration than those of the 'Rubenstein' cultivar, and are larger in size than those of the 'Pixie Meadowhite' cultivar.

The new cultivar of the present invention can be grown to advantage to provide colorful ornamentation in the landscape. It also grows well when potted and can be used to brighten patios, as well as other residential settings.

Asexual reproduction of the new cultivar by the use of tissue culture has been carried out at West Grove, Pa., U.S.A. Such propagation has confirmed that the unique combination of characteristics of the new cultivar has been stably established and is well transmitted to successive generations. The new cultivar asexually reproduces in a true-to-type manner.

The new cultivar has been named 'Conevin' and will be marketed under the PURPLE FANTASY trademark.

BRIEF DESCRIPTION OF THE PHOTOGRAPH

The accompanying photograph shows as nearly true as it is reasonably possible to make the same in a color illustration of this character, a typical flowering container-grown plant of the new cultivar at an age of approximately six months. The plant was grown under production conditions near West Grove, Pa., U.S.A., and the photograph was taken during November 2007.

DETAILED DESCRIPTION

The following is a detailed description of the new cultivar of the present invention which was prepared while observing nine-month old plants growing in containers indoors under production growing conditions near West Grove, Pa., U.S.A. The plants had been forced during the winter and were observed during late March to early April 2008. Color terminology is in accordance with the R.H.S. Colour Chart of The Royal Horticultural Society, London, England, except when general color terms are used which are to be accorded their customary dictionary significance.

Type: Herbaceous perennial for ornamental usage.

Plant:

- *Growth habit.*—Upright with one to several multiple-branched stems.
- *Height.*—Commonly approximately 55 cm on average.
- *Width.*—Commonly up to approximately 62 cm on average.
- *Branching.*—Forms one to several multiple branched stems from a crown or caudex.
- *Stem length.*—Commonly approximately 60 cm on average.
- *Stem diameter.*—Commonly approximately 6 mm on average.
- *Stem color.*—Light yellow green, Yellow-Green Group 144B with some markings of Greyed-Purple Group 183B.
- *Stem texture.*—Slightly rough.
- *Stem strength.*—Relatively strong.
- *Rooting.*—Fibrous.
- *Internodes.*—Longer internodes of approximately 6 cm on average commonly are present from the base to mid-stem, and shorter internodes of approximately 4 cm on average commonly are present from mid-stem to the terminal leaf.

Foliage:

- *Arrangement.*—Alternate.
- *Shape.*—Lanceolate.
- *Size.*—Commonly approximately 13 cm in length on average and approximately 6 cm in width on average.
- *Frequency.*—Commonly up to 12 leaves per stem.
- *Margin.*—Coarsely serrate.
- *Apex.*—Acute.
- *Base.*—Cuneate.
- *Venation.*—Cross-venulate.
- Texture.—Hirsute on the upper leaf surface and lightly hirsute on under leaf surface.
- *Color.*—Commonly near Green Group 137A on the upper surface and between Green Group 137C and 137D on the under surface.
- *Petioles.*—Mostly smooth, commonly of variable length of approximately 5 to 14 cm, approximately 3 mm in diameter, and near Green Group 138B in coloration. Some purple to reddish striation of near Greyed-Purple Group 185C commonly is present on the upper surface of the leaf petioles. Longer petioles commonly are displayed towards the base of the plant. The leaves on the upper approximately one-third of the stems commonly are sessile.

Inflorescence:

- *Season.*—The season of blooming commonly extends from late June through late August or early September at the indicated location.
- *Position.*—The flowers are held above the foliage on strong peduncles and face upright while borne substantially horizontally.
- *Peduncle.*—Commonly approximately 35 to 40 cm in length, approximately 3 to 5 mm in diameter, somewhat rough and hirsute in texture, and between Yellow-Green Group 146C and Yellow-Green Group 146D in coloration.
- *Buds.*—Commonly approximately 2 cm in length, approximately 3.5 cm in diameter, the bud disc color is near Green Group 142B, and the bud ray color is a combination of Yellow-Green Group 145B towards the apex, Red Group 36D at the middle, and Yellow-Green Group 147D towards the base.
- *Flower size.*—Approximately 10.5 cm in diameter on average.
- *Ray florets.*—Lanceolate in shape; notched at the apex, up to approximately 25 in number on average, approximately 4.5 cm in length on average, approximately 1.2 cm in width on average, possess an acute apex with a division at the tip, cuneate base, are Red-Purple Group 70B on the upper surface, and Red-Purple Group 70C on the under surface.
- *Disc florets.*—Approximately 360 in number, the disc commonly is approximately 3 to 4 cm in diameter, the disc commonly is approximately 2 cm in height when the florets are developing, approximately 3.5 cm in height for fully developed flowers, Orange Group 38A in coloration at the apex, and Orange-White Group 159D at the base.
- *Fragrance.*—Light sweet.
- *Lastingness.*—Blossoms commonly last approximately 14 days on the plant under typical growing conditions.
- *Androecium.*—In the disc five per floret, and bear pollen of Yellow-Orange Group 15B.
- *Gynoecium.*—In the disc one per floret, and approximately 5 mm in length.
- *Seeds.*—Fruit and seed development have not been observed during current evaluation.
- *Sepals.*—Each flower commonly includes approximately 75 to 80 sepals, approximately 1.2 cm in length, approximately 3 mm in width, and commonly near Green Group 138A in coloration.
- *Receptacle.*—Commonly approximately 1.5 cm in height on average and approximately 3 cm in diameter on average.

Development:

- *Hardiness.*—U.S.D.A. Hardiness Zone Nos. 3 to 9.
- *Heat tolerance.*—Good.
- *Drought tolerance.*—Good.
- *Disease resistance.*—No particular susceptibility has been noted during observations to date.

The new cultivar has not been observed to date under all possible environmental conditions. Accordingly, it is possible that the phenotype may vary somewhat with variations in the environment, such as temperature, light intensity, day length, and other cultural conditions without variance of the genotype. For instance, plants of the new cultivar when grown in heavy shade commonly tend to have longer petioles that are of a deeper green coloration. Also, the number of flowers commonly will be reduced under such growing conditions.

I claim:

1. A new and distinct *Echinacea* plant having the following combination of characteristics:

(a) forms attractive deeper red-purple flowers than the 'Magnus' cultivar (non-patented in the United States) which are substantially non-fading and bear substantially horizontal ray florets, (b) display an upright branching growth habit, and (c) is well suited for providing attractive ornamentation when grown in the landscape and during pot culture;

substantially as illustrated and described.

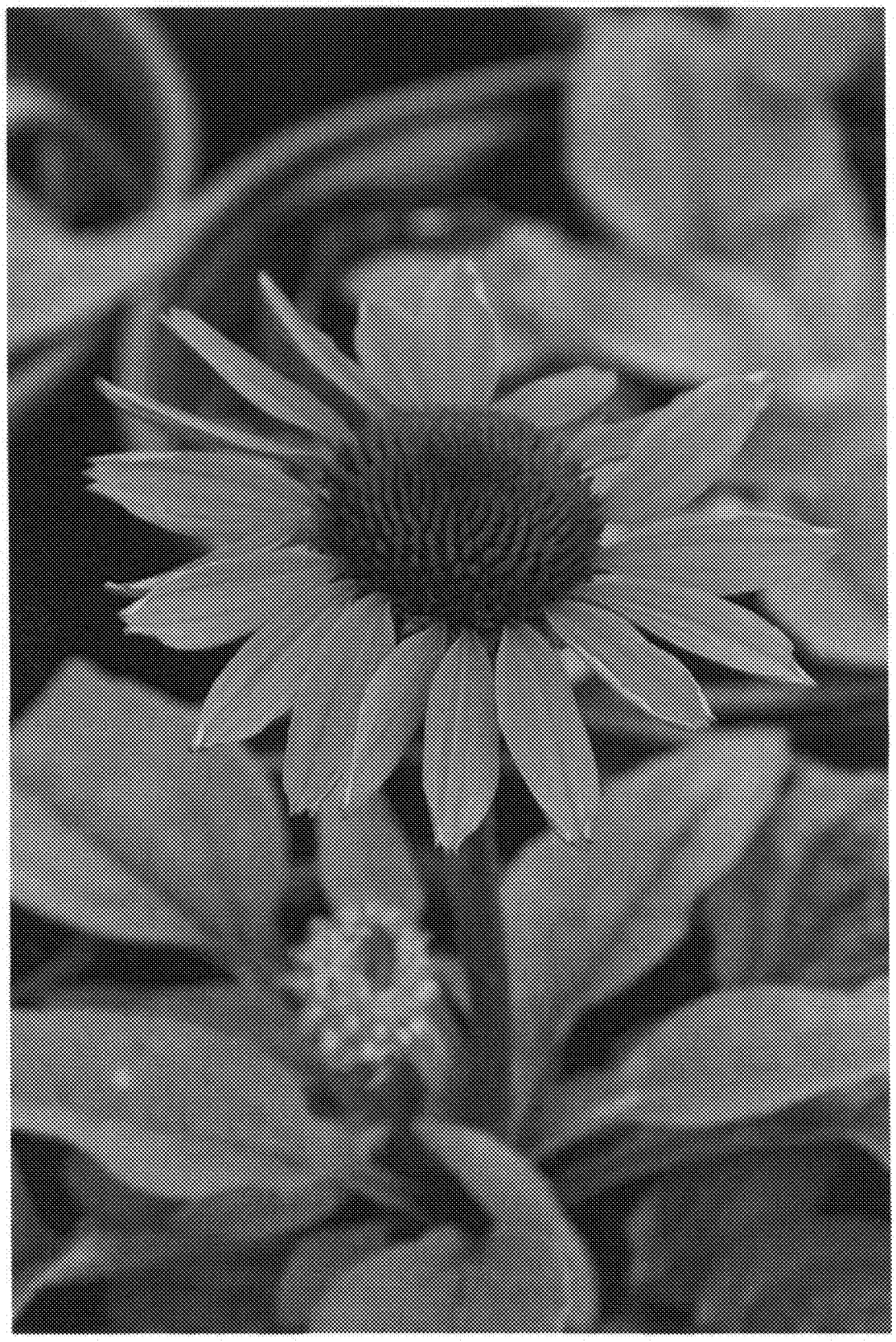

* * * * *